United States Patent [19]

Uber, III et al.

[11] Patent Number: 6,063,052

[45] Date of Patent: May 16, 2000

[54] INJECTION SYSTEM AND PUMPING SYSTEM FOR USE THEREIN

[75] Inventors: Arthur E. Uber, III; Joseph B. Havrilla, both of Pittsburgh; Alan D. Hirschman, Glenshaw, all of Pa.

[73] Assignee: Medrad, Inc., Indianola, Pa.

[ * ] Notice: This patent issued on a continued prosecution application filed under 37 CFR 1.53(d), and is subject to the twenty year patent term provisions of 35 U.S.C. 154(a)(2).
This patent issued on a continued prosecution application filed under 37 CFR 1.53(d), and is subject to the twenty year patent term provisions of 35 U.S.C. 154(a)(2).
This patent is subject to a terminal disclaimer.

[21] Appl. No.: 09/167,069

[22] Filed: Oct. 6, 1998

Related U.S. Application Data

[63] Continuation of application No. 08/655,886, May 31, 1996, Pat. No. 5,827,219, which is a continuation-in-part of application No. 08/144,845, Oct. 28, 1993, Pat. No. 5,569,181.

[51] Int. Cl.[7] .................................................. A61M 1/00
[52] U.S. Cl. ............................................. 604/32; 604/154
[58] Field of Search ............................... 604/65–67, 30, 604/32, 149, 151, 153, 154, 150; 128/DIG. 12

[56] References Cited

U.S. PATENT DOCUMENTS

| | | |
|---|---|---|
| 2,193,177 | 3/1940 | Laythrope . |
| 3,349,713 | 10/1967 | Fassbender . |
| 3,898,983 | 8/1975 | Elam . |
| 3,968,195 | 7/1976 | Bishop . |
| 4,199,000 | 4/1980 | Edstrom . |
| 4,223,675 | 9/1980 | Williams . |
| 4,296,500 | 10/1981 | Monties et al. . |
| 4,340,153 | 7/1982 | Spivey . |
| 4,434,822 | 3/1984 | Bellamy et al. . |
| 4,479,760 | 10/1984 | Bilstad et al. . |
| 4,479,761 | 10/1984 | Bilstad et al. . |
| 4,479,762 | 10/1984 | Bilstad et al. . |
| 4,498,843 | 2/1985 | Schneider et al. ................... 604/65 |
| 4,563,175 | 1/1986 | LaFond . |
| 4,585,009 | 4/1986 | Barker et al. . |
| 4,610,670 | 9/1986 | Spencer . |
| 4,610,790 | 9/1986 | Reti et al. . |
| 4,619,594 | 10/1986 | Moir . |
| 4,634,426 | 1/1987 | Kamen . |
| 4,636,144 | 1/1987 | Abe et al. . |
| 4,750,643 | 6/1988 | Wertrich . |
| 4,781,525 | 11/1988 | Hubbard et al. . |
| 4,783,273 | 11/1988 | Knutsson et al. . |
| 4,835,521 | 5/1989 | Andrejasich et al. . |
| 4,838,860 | 6/1989 | Groshong et al. . |
| 4,857,056 | 8/1989 | Talonn . |
| 4,879,880 | 11/1989 | Harrison . |
| 4,925,444 | 5/1990 | Orkin et al. . |
| 4,943,279 | 7/1990 | Samiotes et al. . |
| 4,946,439 | 8/1990 | Eggers . |
| 4,950,245 | 8/1990 | Brown et al. . |
| 4,978,335 | 12/1990 | Arthur, III . |
| 4,981,467 | 1/1991 | Bobo, Jr. et al. . |
| 5,006,050 | 4/1991 | Cooke et al. . |
| 5,009,654 | 4/1991 | Minshall et al. . |
| 5,044,902 | 9/1991 | Malbec . |
| 5,059,173 | 10/1991 | Sacco . |
| 5,100,380 | 11/1992 | Epstein et al. . |
| 5,116,203 | 5/1992 | Natwick et al. . |
| 5,207,642 | 5/1993 | Orkin et al. . |
| 5,230,614 | 7/1993 | Zanger et al. . |
| 5,303,585 | 4/1994 | Lichte . |
| 5,393,207 | 2/1995 | Maher et al. . |
| B1 5,009,654 | 7/1993 | Minshall et al. . |

FOREIGN PATENT DOCUMENTS

| | | |
|---|---|---|
| 2045070 | 2/1992 | Canada . |
| 0 361 662 | 4/1990 | European Pat. Off. . |
| 0 431 310 A1 | 6/1991 | European Pat. Off. . |
| 0 499 903 A1 | 8/1992 | European Pat. Off. . |
| 36 32 412 | 3/1988 | Germany . |
| 40 02 268 | 1/1991 | Germany . |
| 41 21 568 A1 | 10/1992 | Germany . |
| 43 19 115 | 12/1994 | Germany . |
| 740138 | 11/1955 | United Kingdom . |

OTHER PUBLICATIONS

Debiotech Switzerland, Sales Brochure, Lausanne 9, Switzerland, distributed week of Dec. 1, 1996 at Radiological Society of North America in Chicago, Illinois.
Gelman Sciences Brochure, Nov. 1994, pp. 1–9.
"Powder–metal gerotors for low–cost high–performance pumping", W.H. Nichols Company, pp. 1–8.
"Trust the Best. Gore–Tex PTFE Membrance Vents", W.L. Gore & Associates, 1994.
"Rubber pump spits microliters", Scanning the field for ideas; Medical Industry Focus, Machine Design Feb. 8, 1996.
"Selecting flowmeters", Process Control Course, Part 3., I&CS Mar. 1994, pp. 61–68.
"Nutating Pumps", Operating Principle, Model Specifications, p. 28.
International Search Report for PCT/US 97/07923.

*Primary Examiner*—Wynn Wood Coggins
*Assistant Examiner*—A. T. Nguyen
*Attorney, Agent, or Firm*—Gregory L. Bradley

[57] ABSTRACT

The present invention provides a number of pumping systems and injection systems particularly useful for injecting a liquid medium into a patient. In general, the pumping systems comprise a removable pumping unit. The removable pumping unit includes means for pressurizing the liquid medium via the rotational displacement of the liquid medium. The present invention also provides a pumping system comprising a pumping unit for pressurizing the liquid medium and a feedback-controlled drive means in connection with the pumping unit for providing a controlled powered drive to the pumping unit. The pumping system further comprises a flow meter for measuring the flow rate of the pressurized liquid medium exiting the pumping system and control means in communicative connection with the drive means for providing a control signal to control the powered drive provided to the pumping unit. The control means is suitable to receive a feedback signal from the flow meter corresponding to the flow rate of the pressurized liquid medium exiting the pumping unit. The control signal provided to the drive means is a function of the feedback signal.

28 Claims, 5 Drawing Sheets

INJECTION SYSTEM AND PUMPING SYSTEM FOR USE THEREIN

CROSS-REFERENCE TO RELATED APPLICATIONS

This application is a continuation of application Ser. No. 08/655,886, filed on May 31, 1996, now U.S. Pat. No. 5,827,219, which is a continuation-in-part of application Ser. No. 08/144,845, filed on Oct. 28, 1993, now U.S. Pat. No. 5,569,181 the contents of which are hereby incorporated by reference.

FIELD OF THE INVENTION

The present invention relates to injection systems and pumping systems suitable for injecting a liquid medium, and, particularly, to injection systems and pumping systems for injecting a liquid medium into a body.

BACKGROUND OF THE INVENTION

In many medical procedures, such as drug delivery, it is desirable to inject a fluid into a patient. Likewise, numerous types of contrast media (often referred to simply as contrast) are injected into a patient for many diagnostic and therapeutic imaging procedures. For example, contrast media are used in diagnostic procedures such as X-ray procedures (including, for example, angiography, venography and urography), CT scanning, magnetic resonance imaging (MRI), and ultrasonic imaging. Contrast media are also used during therapeutic procedures, including, for example, angioplasty and other interventional radiological procedures. Regardless of the type of procedure, any fluid injected into the patient must be sterile and contain a minimum of pyrogens.

A number of substantial problems arise in the use of current pumping systems and methods for injecting fluid into a patient's body. For example, it is often difficult to accurately control the pressure and flow rate of the fluid exiting the pumping system. Although peristaltic pumps have long been successfully used in relatively low pressure applications, for example, peristaltic pumps are difficult to control with accuracy.

In the case of relatively high pressure applications, such as CT and angiography, mechanized syringe injectors are used. The use of mechanized syringe injectors also results in a number of substantial drawbacks. Current mechanisms for powering and controlling syringe pumps are complicated, inefficient and costly. Expensive and bulky pressure jackets for housing the syringe pumps are often required to prevent failure at high pressures. Syringe pumps are severely limited in that only the volume of fluid contained in the syringe can be injected at one time. Disposable syringe pumps are costly. Moreover, the rise time of syringe injectors is limited by the inertia of the extensive drive train required to translate motor rotation into syringe plunger motion.

These and other drawbacks in current syringe pumping systems create and magnify a number of inefficiencies in current procedures for injecting contrast media. For example, a number of factors, including, but not limited to, the procedure to be performed and the size of the patient, determine: (i) the contrast to be used, (ii) the concentration thereof, and (iii) the amount to be injected. Under current practice of injecting contrast media via syringe pumping systems, hospitals must purchase and stock many contrast media concentrations in multiple container sizes in an attempt to provide the correct concentration and amount of a specific contrast for a specific procedure, while minimizing the wastage of contrast. In that regard, contrast is typically very expensive.

Thus, most contrast media are provided by manufacturers in numerous concentrations in sterilized containers (such as glass bottles or plastic packages) ranging incrementally in size from 20 ml to 200 ml. These containers are generally designed for a single use (that is, once a container is opened for a patient, it is used for that patient only). The contrast is generally aspirated from such containers via the syringe pump used to inject the contrast, and any contrast remaining in the container is discarded to prevent infection with potentially contaminated contrast. The hospital staff is faced with the task of choosing an appropriately sized contrast container to assure an optimum study while minimizing discarded contrast. Time consuming procedures are required to reload the syringe if more contrast is required than originally calculated. On the other hand, expensive waste results if only a portion of a filled syringe is injected. The inventory of contrast containers required under the current system increases costs and regulatory burdens throughout the contrast media supplier-consumer chain.

Many of these costs, regulatory burdens and other problems associated with the use of multiple contrast containers can be substantially eliminated through use of relatively large contrast media containers for single- and multiple-patient use in connection with a pumping system allowing any volume and concentration of contrast to be injected as determined by the hospital staff before or during a procedure. Current syringe pumping systems simply do not provide a sufficiently cost-effective and efficient pumping system to provide optimal pressurization for injection of contrast and other liquid media.

It is, therefore, very desirable to develop pumping systems that reduce or eliminate the limitations associated with current pumping systems.

Summary of the Invention

The present invention provides a number of pumping systems for use in injecting a liquid medium into a patient. In one embodiment, the pumping system comprises a removable pumping unit. The removable pumping unit preferably comprises a housing having an inlet port for allowing the liquid medium to enter the housing. The housing preferably has disposed therein a means for pressurizing the liquid medium via the rotational displacement of the liquid medium. Although rotational or rotary pumping units have been used in a number of industries, rotary pumping units have not been used in the medical fields in connection with the injection of liquid mediums into patients. The terms "rotary" or "rotational" as used herein in connection with the pumping unit refer to a pumping unit comprising at least one rotatable member within the housing for contacting and pressurizing the liquid medium via rotational displacement thereof. The housing of the pumping unit also comprises an outlet port through which the pressurized liquid medium exits the housing. The removable pumping unit is removably connected to a drive means for providing a powered rotational drive to the pressurizing means.

The pumping unit is preferably readily removable from connection with the drive means to preferably enable disposal of the pumping unit and replacement with another removable pumping unit when desired. For example, the removable pumping unit of the present invention may be discarded and replaced at predetermined intervals such as after each injection procedure or after emptying of a contrast container or after a specified time has elapsed.

The present invention also provides an injection system comprising a pumping system as described above. Such an injection system preferably comprises a liquid medium container in fluid connection with the pumping unit of the pumping system. Means for detecting air bubbles and/or means for removing such air bubbles may be placed in the fluid path before the pumping unit to assist in detecting or eliminating air bubbles from the medium before the medium reaches the pumping system. The injection system preferably includes, in fluid connection with the outlet port of the pumping unit, a disposable patient interface in contact with the patient for injection of pressurized medium into the patient.

The output of the pumping unit is also preferably in fluid connection with a check valve for substantially ensuring unidirectional flow of the medium and thereby substantially preventing contamination of the pumping unit with body fluids. Such check valve is placed inline prior to the patient interface.

The present rotary pumping system and injection systems comprising such pumping system offer a number of substantial advantages over current syringe pump injection systems. For example, the present pumping system: (i) separates the function of contrast storage from contrast pressurization; (ii) simplifies mechanics and control; (iii) provides for utility with present contrast containers while being easily adaptable to other types of containers; (iv) minimizes contrast wastage; (v) reduces injector head mechanical complexity and size; (vi) greatly reduces drive train inertia and thereby improves system performance; and (vii) minimizes the mass of plastic discarded for each procedure. Moreover, concerns associated with cross-contamination with the use of multi-patient contrast containers are substantially reduced.

The present invention also provides a pumping system comprising a pumping unit for pressurizing the liquid medium and a feedback-controlled drive means in connection with the pumping unit for providing a controlled powered drive to the pumping unit. The pumping system further comprises a flow meter for measuring the flow rate of the pressurized liquid medium exiting the pumping unit and control means in communicative connection with the drive means for providing a control signal to control the powered drive provided to the pumping unit. The control means is suitable to receive a feedback signal from the flow meter corresponding to the flow rate of the pressurized liquid medium exiting the pumping unit. The control signal provided to the drive means is responsive to (that is, a function of) the feedback signal.

The provision of a flow meter and feedback control therefrom in a pumping system enables more accurate control over the flow rate of pressurized fluid exiting the pumping system than possible with current pumping systems in the medical and other arts. Moreover, a flow meter and feedback control enables fabrication of pumping units (whether rotary pumping units or other pumping units) with manufacturing or machining tolerances much less strict or "looser" than currently required to maintain suitable control. This loosening of manufacturing tolerances enables the fabrication of much less expensive pumping systems of all types.

DETAILED DESCRIPTION OF THE INVENTION

Figure 1:
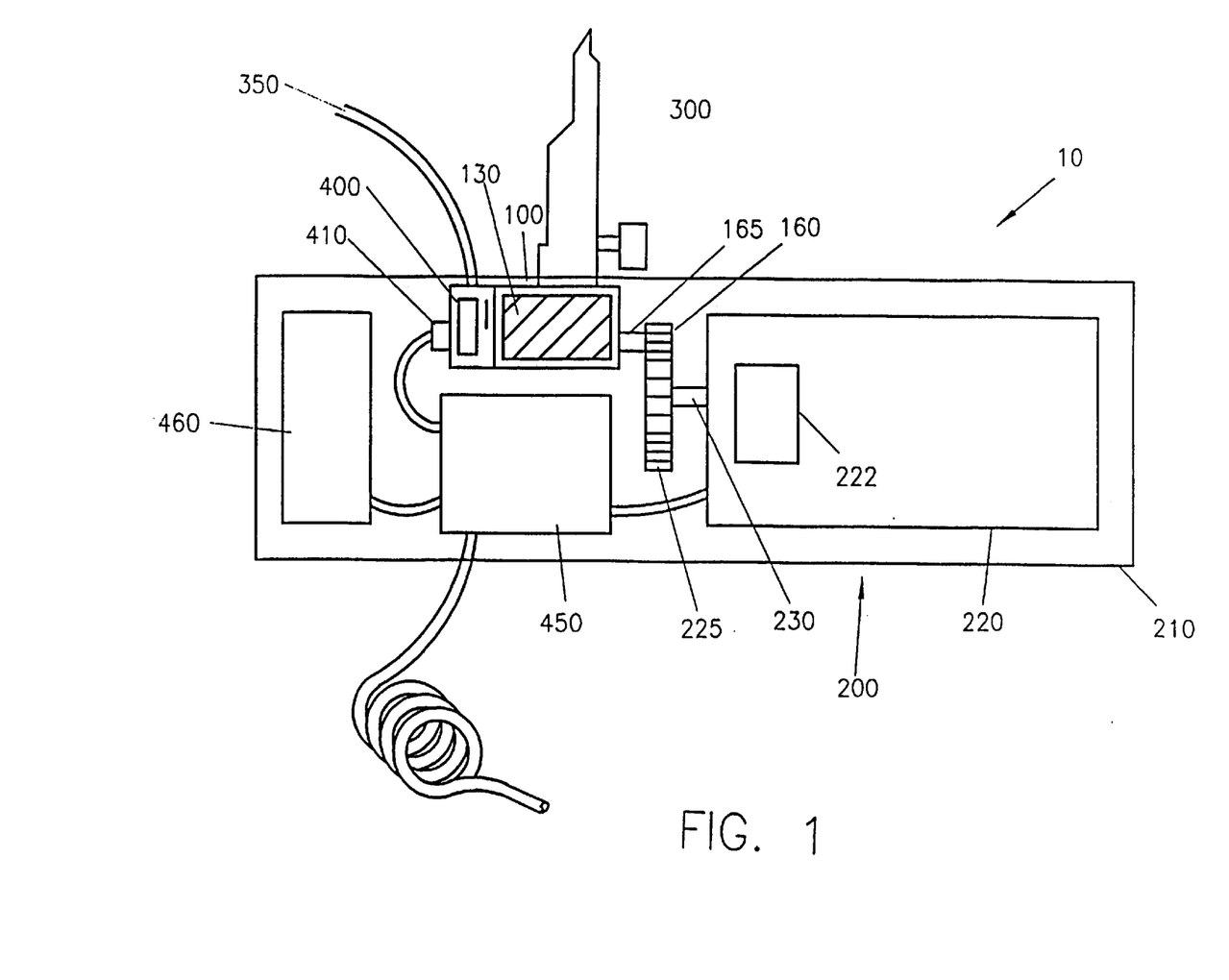
FIG. 1 illustrates an embodiment of a pumping system of the present invention.
Figure 2:
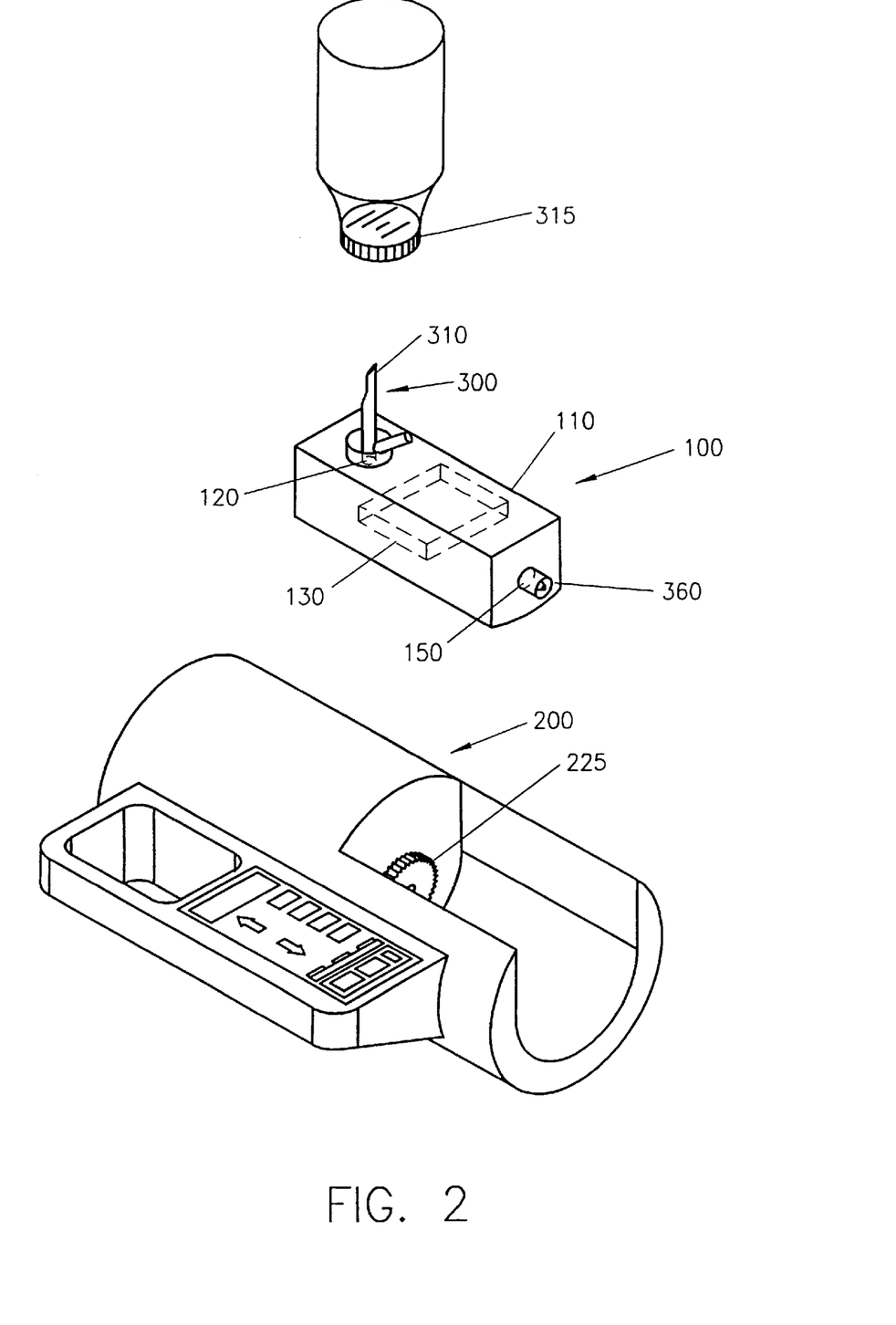
FIG. 2 illustrates an embodiment of a pumping system including controls and a handle, wherein the removable pump unit slides into the front of an injector head.
Figure 3:
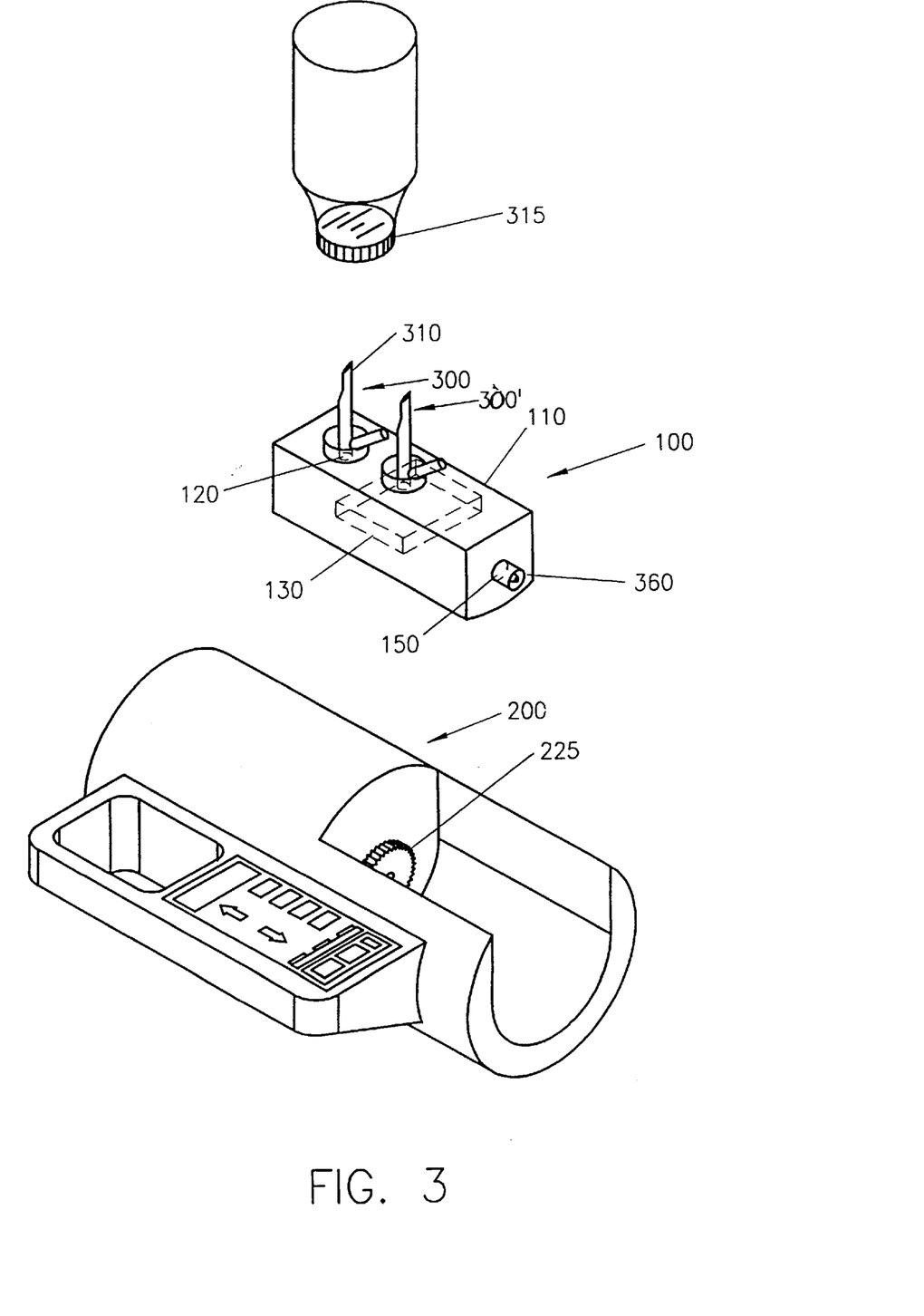
FIG. 3 illustrates another embodiment of a pumping system of the present invention comprising multiple inlet connections.

As illustrated in FIGS. 1 through 3, pumping system 10 comprises a removable pumping unit 100. Removable pumping unit 100 preferably comprises a housing 110 having an inlet port 120 for allowing a liquid medium such as a contrast medium or contrast to enter housing 110. As best illustrated in FIG. 2, housing 110 preferably has disposed therein pressurizing means 130 for pressurizing the liquid medium. Pressurizing means 130 preferably operate via the rotational displacement of the liquid medium. Housing 110 also comprises an outlet port 150 through which the pressurized liquid medium exits housing 110 for injection into the patient. Pressures ranging from approximately 300 psi in CT to approximately 1200 psi in angiography are readily achieved with pumping system 10. In that regard, rotational displacement of the liquid medium provides an efficient mechanism for achieving those pressures and even higher pressures. Moreover, pumping system 10 provides an efficient mechanism for use in low pressure medical applications as well.

As best illustrated in FIG. 1, during operation removable pumping unit 100 is in operative connection with drive means 200 for providing a powered rotational drive to pressurizing means 130. Pumping unit 100 is removable from connection with drive means 200 to preferably enable disposal of pumping unit 100 and replacement with another removable pumping unit 100 when desired. Preferably, pumping unit 100 is readily removable from connection with drive means 200, for example, via gear 160 as described below. In that regard, removal of pumping unit 100 from connection with drive means 200 preferably requires no tools and can be accomplished by the operator in a relatively short period of time.

Drive means 200 preferably includes a durable housing 210 enclosing a drive motor 220. Drive means 200 also includes means for removably coupling or connecting to a cooperating connection means on pumping unit 100. In one embodiment, for example, drive motor 220 preferably drives a gear 225 via drive shaft 230. Gear 225 preferably mates with a corresponding gear 160 on pumping unit 100. Pressurizing means 130 are in operative connection with gear 160 via shaft 165. In general, such mating gears (that is, gear 225 and gear 160) are suitable to provide all required speed reduction.

In an alternative embodiment, an electrical clutch 222 can be incorporated into drive motor 220 or placed between drive motor 220 and gear 225. For injectors such as cardiac angiography, in which it is beneficial to have a very short injection with a relatively quick start and a relatively quick stop, drive motor 220 can be rotating at the desired speed with electrical clutch 222 disengaged so that gear 225 does not turn. Electrical clutch 222 can then be engaged for the desired length of time, resulting in a very quick rise in the fluid flow upon engagement. This embodiment also permits very quick stops in injection (upon disengagement of electrical clutch 222) which are beneficial during short injection procedures.

A number of common rotational pumps such as centrifugal pumps, rotary vane pumps, gear pumps and nutating pumps are suitable for use in the present invention. In high pressure procedures, gear pumps and rotary vane pumps are preferred. Gear pumps, for example, are commonly used for viscous fluids in arts other than the medical arts. For example, many automobile oil pumps are gear pumps. Currently available gear pumps can achieve pressures of thousands of pounds per square inch (psi) and are commonly used in hydraulic power systems. However, these tend to be metal pumps with closely machined tolerances and are thus relatively expensive.

Pumping unit 100 is quite different from current gear pumps, however, in that it is readily removably connected to drive means 200 and, therefore, easily disposable. Moreover, metal components within pumping unit 100 are undesirable because of their expense and because of the risk of injecting a patient with metal particles.

The materials for housing 110 should exhibit sufficient tensile strength to sustain the desired pressure. Moreover pressurizing means 130 and housing 110 are preferably fabricated from materials suitable to form a compression seal therebetween as common in rotary pumping units. This result can be accomplished using a combination of hard and soft plastics. In addition to having structural characteristics suitable to create sufficient pressurization, those components of pumping unit 100 that contact the liquid medium are preferably fabricated from a material or materials that are "chemically compatible" with the medium. For example, the material(s) should maintain their structural integrity when in contact with the medium and preferably do not leach an amount of any substance into the medium which will impair the functionality of the medium. The fabrication materials are also preferably "biochemically compatible" with the medium. For example, the fabrication materials should not leach an amount of any substance into the medium that will endanger the patient (animal or human) into which the medium is to be injected. Materials suitable for fabrication of housing 110 and pressurizing means 130 include, but are not limited to, polymeric materials such as TPX, polycarbonate and Teflon®-coated polycarbonate. In general, lubricating oils and elastomeric materials should be avoided.

An example of a suitable design for pumping unit 100 is that of gerotors available from W. H. Nichols Company of Portland, Me. The design of such gerotors, including relations for calculating the required specifications therefor are provided in "Powder-Metal Gerotors for Low-Cost High-Performance Pumping," distributed by W. H. Nichols Company. Another example of a suitable design for pumping unit 100 is provided by nutating pumps such as the Model 20510 Nutating Pump available from Gorman-Rupp Industries.

Figure 4A:
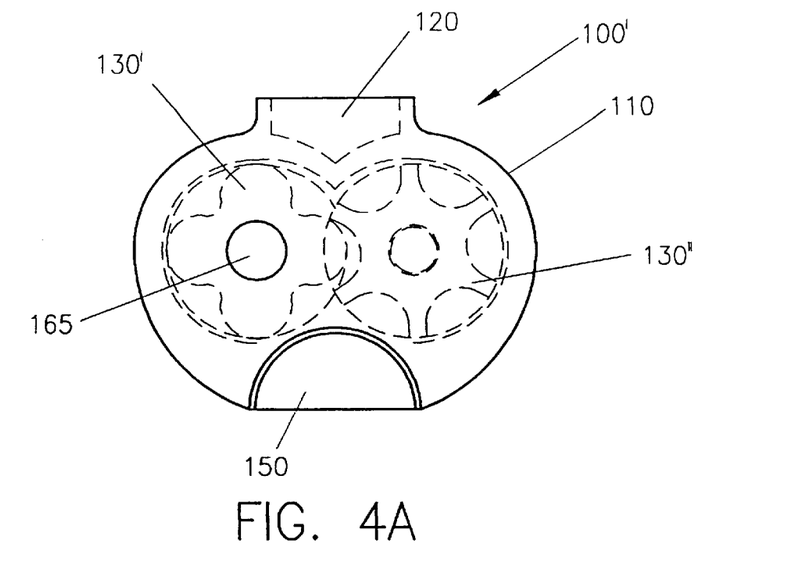
FIGS. 4A and 4B illustrate an embodiment of a removable rotary pumping unit of the present invention.
Figure 4B:
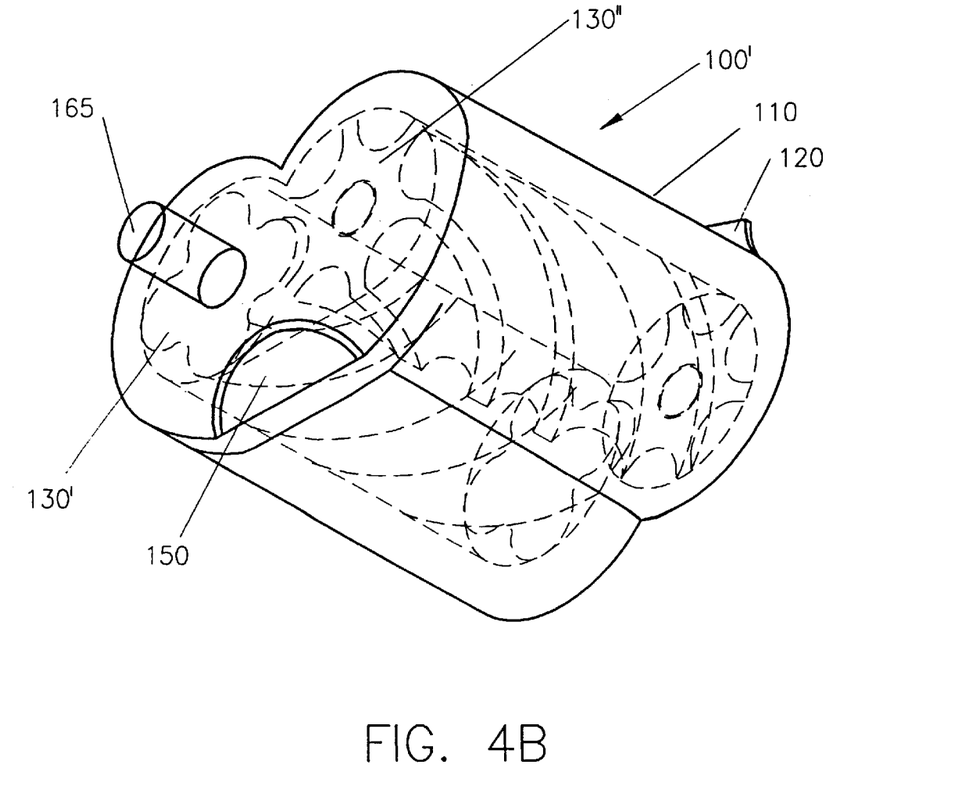

An additional embodiment of a gear pump 100' suitable for use in the present invention is illustrated in FIGS. 4A and 4B. Contained within housing 110 of gear pump 100' are pressurizing means comprising two cooperating pressurizing gears 130' and 130". Shaft 165 is connected with gear 160 (see FIG. 1) which cooperates with gear 225 of drive means 200 to provide a powered drive to pressurizing gears 130' and 130". The fluid medium enters gear pump 100' via inlet port 120, while pressurized fluid medium exits gear pump 100' via outlet port 150.

The interior of housing 110 of pumping unit 100 is preferably connected to an inlet connection 300 (for example, a solid tube) via inlet port 120. Inlet connection 300 may be integral with housing 110 or removably connectable thereto. A distal end of inlet connection 300 is preferably suitable for connection to a contrast medium source for the supply of contrast to pumping unit 100. In one embodiment, inlet connection 300 comprises a spike 310 on a distal end thereof that is suitable to puncture a rubber 315 seal of a contrast container. Preferably, spike 310 is sufficiently long such that air vented into a non-collapsible contrast bottle does not generate bubbles that can be picked up by pumping unit 100. As known in the art, vents are generally required in inlet connection 300 when contrast is drawn from a non-collapsible container to allow sterile air to replace the fluid withdrawn and to prevent creation of a vacuum within the container.

Alternatively, spike 310 can be replaced by a luer connection for use with a contrast container fitted with a corresponding luer connection as known in the medical arts. The distal end of inlet connection 300 can also be connected to a capped container (not shown) so that medium can be poured into the capped container from several smaller contrast containers. Volumetric indicators such as a float and volume markings can be provided to show the amount of fluid in the container.

As clear to those skilled in the art, modifications to inlet connection 300 can easily be made to allow fluid to be drawn from two contrast sources simultaneously or in sequence. As illustrated in FIG. 3, for example, more than one inlet connection 300 and 300' may be provided for connection to multiple contrast containers. Inlet connections 300 and 300' may be connected via a T connection with float balls to take fluid from two contrast bottles. A flushing fluid such as a saline solution may also be introduced via second connection 300' to displace any contrast remaining in the contrast container. Similarly, two container connections can be provided with an injector controlled stopcock at the T connection to provide a flush after injecting or a "Keep-Vein-Open" or "KVO" function. In a KVO function, a relatively low flow rate is maintained to prevent clotting on the needle tip of the contrast needle where the needle is inserted into the blood stream. To provide adequate mixing in the case of two different liquids, two pumps may be required if the liquids to be mixed have significantly different viscosities.

Outlet connection 350 can be integral with outlet port 150 or removably connectable thereto. As illustrated in FIGS. 2 and 3, outlet connection 350 (for example, a connector tube) may be connected to outlet port 150 via a luer connection 360. As housing 210 may be fabricated to be quite small and light in the present invention, outlet connection 350 may be relatively short in length (for example, approximately one foot) and the injector can be placed near the patient's arm. Alternatively, housing 210 can be mounted some distance from the patient (to ensure, for example, that housing 210 doesn't tip over), thereby requiring a longer outlet connection 350 such as a coiled connector tube. Still further housing 210 can be designed to be hand-held by an operator (see FIGS. 2 and 3).

A relatively small, removable gear pump is sufficient for use in pumping system 10. With a maximum flow rate of 10 ml/s, and a motor speed of 3600 rpm, for example, the pump must displace only 0.167 ml/revolution. A set of gears approximately 1 cm long, having a 0.5 cm diameter, and having 16 teeth with a 0.5 mm$^2$ open area is sufficient for such a displacement rate. Therefore, pumping unit 100 can be designed to be less than one-half inch on a side.

In certain medical injection procedures, it is essential that pressure and/or constant flow rate be maintained substantially at a predetermined value during the procedure substantially independent of (1) changes in input or output resistances and (2) changes in fluid viscosity. Current syringe pumps are positive displacement pumps, which means that the fluid is positively (or absolutely) displaced (or pumped) as the syringe plunger is moved. Rotary pumps such as gear pumps typically experience some "blow by", which is generally defined as fluid that leaks between the tip of the gear teeth and the pump housing to travel in a direction reverse to the principle flow. As a result of blow by, the calibration of pumping unit 100 (typically in ml of fluid per revolution) depends slightly on the pressure at outlet port 150. Although it may be possible to design a limited life plastic pump with strict tolerances and substantially no blow by, it is likely that such a unit would be capable of pumping air. If the tolerances are relaxed to provide some clearance between the gears and the pump housing, the pump is easier to make and air is difficult to pump, but the calibration accuracy of the pump will once again depend upon pressure at its outlet.

To enable relaxation or loosening of the tolerances required for the components of pumping unit 100, as shown in FIG. 1, the output of drive motor 220 is preferably controlled via control means 450 in communicative connection with drive motor 220. To achieve a flow rate accuracy independent of pressure, pumping system 10 preferably comprises a flow meter 400 for measuring the flow rate of fluid exiting pumping unit 100. Preferably, the components of flow meter 400 that contact the pressurized liquid are readily removable and disposable. As illustrated in FIG. 1, flow meter 400 is preferably integral with pumping unit 100. It is also possible, however, for flow meter 400 to be separate from pumping unit 400, with a fluid path connection being made between flow meter 400 and pumping unit 100. Flow meter 400 may comprise, for example, a set of disposable polymeric gears which are turned by the fluid flow. Flow meter 400 is preferably positioned in the flow of the liquid medium near outlet port 150. In one embodiment, the rotation of flow meter 400 is sensed by one or more LED/phototransistor pairs 410.

Many types of flow meters 400 can be used in the present invention. In cases in which accurate readings are required even at low flow rates, positive displacement flow meters are preferred. For many medical imaging applications however, low flow rates are not used and flow meters other than positive displacement flow meters (for example, turbine flow meters) can be used. Thermal mass flow meters can also be used. Thermal mass flow meters can also act as fluid heaters. A number of flow meters for use in the present invention are available from the Cole-Palmer Company of Niles, Ill. Moreover, a detailed discussion of flow meters is presented in "Selecting Flowmeters," *Instrument and Control Systems* (March 1994), the disclosure of which is incorporated herein by reference.

The output signal of flow meter 400 is preferably transmitted to and used by a servo control mechanism of control means 450 to provide a feedback signal to control the speed of drive motor 220. Such control will substantially loosen the required tolerances on the gear pump. The servo control mechanism is preferably microprocessor controlled as well known in the control arts. Servo control mechanisms suitable for the present use are commercially available from Galil, Inc. of California.

Servo feedback control in currently available injectors is based upon the position of the syringe plunger used to pressurize the liquid medium to be injected by such systems. In these systems, the actual flow rate is somewhat indeterminate and lags the movement of the plunger as a result of mechanical tolerances and fluid path capacitance. In pumping system 10, however, actual flow rate is measured. Therefore, control can be more precise than possible with current systems. Although the servo control of pumping system 10 must account for the fluid inertia, the total inertia and capacitance are significantly reduced over that in currently available systems, which typically comprise a motor, a gear train, a ball screw, and a syringe with pressure expansion.

During use, removable pumping unit 100 is, for example, slid or clipped into place within pumping system 10. A fluid container is then connected to pumping system 10. The container can be taken directly from a heater box. Warm contrast is more comfortable to the patient and less viscous than cool contrast, making it easier to pump. The fluid is preferably advanced slowly, using a control on pumping system 10 to remove air from inlet connection 300 and pumping unit 100. Outlet connection 350 is then connected to pumping unit 100, cleared of air and connected to the patient and the injection is initiated. After the injection procedure, removable pump unit 100, and connections 300 and 350 may be removed and disposed of.

The present invention also provides an injection system 600 comprising pumping system 610 as described above. Injection systems well suited for use with pumping system 10 are discussed in U.S. patent application Ser. No. 08/144, 845. An embodiment of an injection system 600 of the present invention is illustrated schematically in FIG. 5. As illustrated, injection system 600 preferably comprises a liquid medium container 617 in fluid connection with pumping system 610. Preferably, means for detecting air bubbles 620 and/or means for removing such air bubbles 630 are placed in fluid connection with the medium container before pumping unit 615 such that the air bubbles are removed from the medium before the medium reaches pumping unit 615. Detection means 620, for example, can be an ultrasonic sensor such as that available from Zevex of Salt Lake City, Utah, or Introtek of Edgewood, N.Y. Air-eliminating filters suitable for use in the present invention as air removing means 630 are available, for example, from Gelman Sciences, Inc. of Ann Arbor, Mich. Air removing means 630 may also comprise a Gore-Tex® PTFE Membrane Vent available from W. L. Gore & Associates, Inc of New Jersey. Because such devices often cannot detect small air bubbles and consequently do not operate well at high pressure, detection means 620 and/or removing means 630 are preferably located before pumping unit 100 of pumping system 10 so that any bubbles within the fluid stream will be as large as possible.

Another method of reducing the risk of pumping air via pumping unit 100 is through appropriate design of tolerances/clearances in pressurizing means 130. In that regard, by adjustment of the tolerances of pressurizing means 130 such that some of the fluid flows reverse to the principal flow (that is, some of the fluid experiences blow by), the risk of pumping air can be substantially reduced. An example of one manner of creating blow by is provided in U.S. Pat. No. 3,349,713, the disclosure of which is incorporated herein by reference. As set forth in U.S. Pat. No. 3,349,713 a portion of a gear tooth can be beveled to allow a portion of the fluid within the pump housing to flow reverse to the principal flow. In effect, the tolerance of the gear is loosened. As clear to one skilled in the art, the amount of blow by is easily controlled by selecting the tolerance of the pressurizing means 130. In general, if pumping unit 100 (when designed for sufficient blow by) tries to pump air (for example, if the contrast supply container is empty), the pressure required to turn flow meter 400 will be sufficiently high that the air simply blows by the gear and the housing in pumping unit 100. In this case, the pumping action will be defeated. Air is difficult to pump in the case of blow by because the viscosity of air is much less that of injection liquids. Even a small percentage of blow by will significantly reduce the pressure pumping unit can develop when attempting to pump air.

A further method to reduce the risk of pumping air is to design pump unit 100 to have an amount of "carry back." Carry back refers to fluid that remains (for example, in the meshed gear teeth of a gear pump) and is brought from the outlet of the pumping unit back to the inlet in the normal course of operation. Liquids are substantially incompressible, whereas gasses are very compressible. Therefore, the amount of gas carried back is a function of pump outlet pressure, whereas the amount of liquid carried back is substantially independent of outlet pressure. If, for example, the volume carried back is 50% of the volume carried forward, the pump can develop a desired pressure of 300 psi with the liquid to be injected, but can develop no more than 15 psi with a gas. The inability to pump air resulting from carry back is independent of blow by. Therefore, a pump with strict tolerances and no flow meter can have sufficient carry back to substantially eliminate the risk of pumping air. For example, a valve can be provided that requires at least 15 psi to open and allow flow, and thus air will not develop sufficient pressure to open the valve.

Bubbles can be pumped with the fluid, however. It is thus preferable to clear bubbles from the fluid path. Bubble removal is simplified by avoiding bubble creation during filling by designing pumping unit 100 so that bubbles will easily flow out as fluid is put in. While designing pumping unit 100 to allow substantial blow by reduces the risk of pumping air, the loosened tolerances of pumping unit 100 result in pump inefficiency. As described above, however, suitable control may be maintained over pumping unit 100 via a flowmeter and feedback control.

Figure 5:
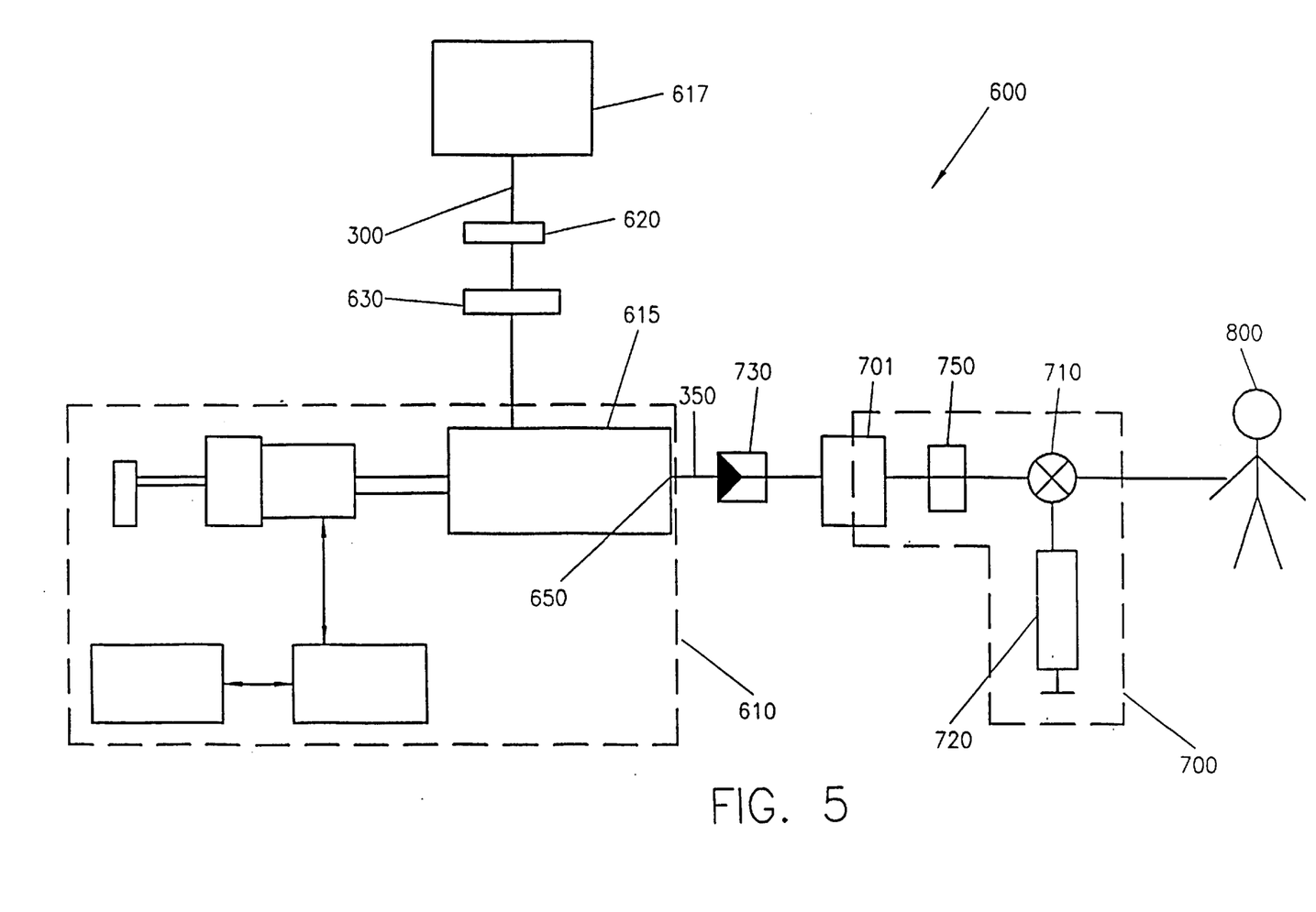
FIG. 5 illustrates an embodiment of an injection system incorporating the pumping system of the present invention.

Injection system 600 also preferably includes (in fluid connection with outlet port 650 of the pumping unit 615) a disposable patient interface 700 in contact with a patient 800 for injection of the medium into patient 800. Patient interface preferably includes a three-way stopcock 710 and a hand-operated syringe 720. In connection with stopcock 710, syringe 720 may be used to draw blood from the patient, for example, to verify good intravenous catheter placement in CT and to purge any small bubbles of air that might occur connection 710 with the vascular catheter. Syringe 720 may also be used to inject fluids other than the medium (for example, medications). Further, syringe 720 can be filled with medium for test injections during angiography. Patient interface 700 is preferably disposed of after each procedure.

Before reaching patient interface 700, the output of pumping unit 615 is preferably in fluid connection with a check valve 730 for substantially ensuring unidirectional flow of the medium and thereby substantially preventing contamination of pumping unit 615 with body fluids. Check valve 730 may comprise, for example, a spring-loaded ball valve or a duck bill valve. The need for check valve 730 may be eliminated by providing the pump unit drive shaft with means for preventing reverse rotation thereof. For example, the drive shaft (not shown) of pumping unit 615 can be provided with detents or stops (not shown) to prevent reverse rotation, or the flow meter mechanics may be designed in a similar way so that they cannot be turned in a reverse direction. Prior to reaching patient interface 700, the effluent of pumping unit 615 is preferably in fluid connection with filter means 750 for removing particles from the medium. As shown in FIG. 5, filter means 750 is disposable as it may become contaminated, and is part of patient interface 700.

In certain embodiments it may be desirable to include means for limiting or stopping flow of the injection medium if the developed pressure exceeds a certain threshold pressure, for example to prevent failure of the intravascular catheter. This result can be accomplished in a number of manners including the inclusion of means for sensing pressure in connection with the outlet of pumping unit 100. Such a pressure sensor would have to be sterilizable and/or disposable, however. In another embodiment, as illustrated in FIG. 1, means 460 for measuring motor current are provided so that motor current of drive motor 220 can be measured as an indirect measurement of pressure. Such indirect measurements of fluid pressure via motor current are performed in a number of currently available syringe injector systems. Although blow by at higher pressures may create a deviation from a linear relation between motor current and pressure, the flow rate measured by flow meter 400 can be combined with the measurement of motor current through an algorithm to estimate true pressure. As clear to one skilled in the art, a calibration curve can be used by the algorithm to correct for such non-linearity.

Although the present invention has been described in detail in connection with the above examples, it is to be understood that such detail is solely for that purpose and that variations can be made by those skilled in the art without departing from the spirit of the invention except as it may be limited by the following claims.

What is claimed is:

1. A removable pumping unit for use with at least one container of liquid medium and a drive housing for receiving the removable pumping unit, the drive housing comprising drive means for powering the removable pumping unit, the removable pumping unit comprising:

a chamber comprising at least one inlet port for allowing liquid medium to enter said chamber from the at least one container and an outlet port through which the liquid medium exits said chamber;

a rotary mechanism disposed in said chamber and in fluid contact with the liquid medium, said chamber and said rotary mechanism cooperable to pressurize the liquid medium via rotational displacement thereof for pressurized injection into a patient; and a drive connector operatively associated with said rotary mechanism, said drive connector removably coupling said rotary mechanism to the drive means of the drive housing.

2. The removable pumping unit of claim 1 wherein the removable pumping unit is fabricated from a polymeric material which is chemically and biochemically compatible with the liquid medium.

3. The removable pumping unit of claim 1 wherein the rotary mechanism is adapted to allow a portion of the liquid medium within the chamber to flow in a direction reverse to the principal flow direction to reduce the risk of pumping air into the patient.

4. The removable pumping unit of claim 1, further comprising a flow meter for measuring the flow rate of the pressurized liquid medium exiting the removable pumping unit and control means in connection with the drive means for providing a control signal to control the powered drive provided to the pumping unit, the control means being in communicative connection with the flow meter to receive a feedback signal from the flow meter corresponding to the flow rate of the pressurized liquid medium exiting the pumping unit, the control signal being responsive to the feedback signal.

5. The removable pumping unit of claim 1, further comprising means for preventing pressure of the pressurized medium from exceeding a predetermined pressure.

6. A removable pumping unit for use with a drive housing for receiving the removable pumping unit, the drive housing comprising drive means for powering the removable pumping unit, the removable pumping unit comprising:
   a chamber comprising at least one inlet port for allowing liquid medium to enter said chamber from at least one container and an outlet port through which the liquid medium exits said chamber;
   a rotary mechanism disposed in said chamber and in fluid contact with the liquid medium, said rotary mechanism allowing at least a portion of the liquid medium within said chamber to flow in a direction reverse to the principal flow direction to reduce the risk of pumping air into a patient; and
   a drive connector operatively associated with said rotary mechanism, said drive connector removably coupling said rotary mechanism to the drive means of the drive housing.

7. The removable pumping unit of claim 6, further comprising means for detecting air bubbles in the liquid medium placed in fluid connection with the container before the removable pumping unit.

8. The removable pumping unit of claim 6, further comprising means for substantially eliminating air bubbles from the liquid medium placed in fluid connection with the container before the removable pumping unit such that air bubbles are substantially eliminated from the liquid medium before the liquid medium reaches the pumping unit.

9. The removable pumping unit of claim 6, further comprising valve means in fluid connection with the outlet port of the pumping unit for substantially ensuring unidirectional flow of the liquid medium, the valve means being placed before a patient interface.

10. The removable pumping unit of claim 6, further comprising means in fluid connection with the outlet port of the pumping unit for substantially removing air bubbles from the liquid medium, the removing means being placed before a patient interface.

11. The removable pumping unit of claim 6 wherein the removable pumping unit is fabricated from a polymeric material which is chemically and biochemically compatible with the liquid medium.

12. The removable pumping unit of claim 6, further comprising a flow meter for measuring the flow rate of the pressurized liquid medium exiting the removable pumping unit and control means in connection with the drive means for providing a control signal to control the powered drive provided to the pumping unit, the control means being in communicative connection with the flow meter to receive a feedback signal from the flow meter corresponding to the flow rate of the pressurized liquid medium exiting the pumping unit, the control signal being responsive to the feedback signal.

13. The removable pumping unit of claim 6, further comprising means for preventing pressure of the pressurized medium from exceeding a predetermined pressure.

14. A pumping system comprising:
   a removable pumping unit for pressurizing a liquid medium, the pumping unit comprising: a chamber comprising an inlet port for allowing a liquid medium to enter the chamber and an outlet port through which the liquid medium exits the chamber; a rotary mechanism disposed in the chamber and in fluid contact with the liquid medium, the chamber and the rotary mechanism cooperable to pressurize the liquid medium via rotational displacement thereof for pressurized injection into a patient; and a drive connector operatively associated will the rotary mechanism;
   a drive housing for receiving said removable pumping unit, the drive housing comprising drive means for powering the rotary mechanism, the drive means comprising a drive coupling for removably coupling the rotary mechanism to the drive connector on said pumping unit for providing a powered drive to said pumping unit;
   a flow meter in fluid communication with the liquid medium, said flow meter operable to measure the flow rate of the pressurized liquid medium exiting said pumping unit; and
   a control system in communication with said flow meter and drive means, said control system operable to receive a feedback signal from the flow meter corresponding to the flow rate of the pressurized liquid medium exiting said pumping unit and to generate a control signal responsive to the feedback signal to control the powered drive provided to said pumping unit, said flow meter and the control system cooperable to maintain a desired flow rate substantially independent of changes in input and output flow resistance and changes in the viscosity of the liquid medium.

15. A method of using a pumping unit to inject a liquid medium into a patient, comprising:
   providing a disposable pumping unit for pressurizing the liquid medium, the pumping unit comprising a chamber comprising at least one inlet port for allowing the liquid medium to enter the chamber and an outlet port through which the liquid medium exists the chamber, a rotary mechanism disposed in the chamber and in fluid contact with the liquid medium, the chamber and the rotary mechanism cooperable to pressurize the liquid medium via rotational displacement thereof for pressurized injection into the patient, and a drive connector operatively associated with the rotary mechanism;
   providing a drive housing for receiving the disposable pumping unit, the drive housing comprising drive means for powering the rotary mechanism, the drive means comprising a drive coupling for removably coupling the rotary mechanism to the drive connector on the pumping unit for providing a powered drive to the rotary mechanism;
   connecting the disposable pumping unit to the drive housing;
   providing at least one container of liquid medium;
   connecting the at least one liquid medium container to the at least one inlet of the disposable pumping unit;
   providing a disposable patient interface having first and second ends;
   connecting the first end of the disposable patient interface to the outlet port of the disposable pumping unit;
   connecting the second end of the disposable patient interface to the patient;
   activating the drive means to power the rotary mechanism; and
   injecting liquid medium into the patient through the disposable patient interface.

16. The method of claim 15, further comprising:

deactivating the drive means to terminate the injection of liquid medium into the patient;

disconnecting the second end of the disposable patient interface from the patient;

disconnecting the first end of the patient interface from the outlet port of the disposable pumping unit; and disposing of the disposable patient interface.

17. The method of claim 16, further comprising:

providing a second disposable patient interface having first and second ends;

connecting the first end of the second disposable patient interface to the outlet port of the disposable pumping unit;

connecting the second end of the second disposable patient interface to the patient;

activating the drive means to power the rotary mechanism;

injecting liquid medium into the patient through the second disposable patient interface;

deactivating the drive means to terminate the injection of liquid medium into the patient;

disconnecting the second end of the second disposable patient interface from the patient;

disconnecting the first end of the second patient interface from the outlet port of the disposable pumping unit; and disposing of the second disposable patient interface.

18. The method of claim 15, further comprising:

disconnecting the at least one liquid medium container from the at least one inlet port of the disposable pumping unit;

disconnecting the disposable pumping unit from the drive housing; and disposing of the disposable pumping unit.

19. The method of claim 18, further comprising:

providing a second disposable pumping unit;

connecting the second disposable pumping unit to the drive housing; and connecting the at least one liquid medium container to the at least one inlet port of the second disposable pumping unit.

20. The removable pumping unit of claim 1 wherein the at least one inlet port comprises two inlet ports and the at least one container comprises two containers, each inlet port being in fluid communication with a respective container.

21. The removable pumping unit of claim 1, further comprising means for detecting air bubbles in the liquid medium placed in fluid connection with the container before said chamber.

22. The removable pumping unit of claim 1, further comprising means for substantially eliminating air bubbles from the liquid medium placed in fluid connection with the container before said chamber such that air bubbles are substantially eliminated from the liquid medium before the liquid medium reaches said chamber.

23. The removable pumping unit of claim 1, further comprising valve means in fluid connection with the outlet port of said chamber for substantially ensuring unidirectional flow of the liquid medium, the valve means being placed before a patient interface.

24. The removable pumping unit of claim 1, further comprising means in fluid connection with the outer port of said chamber for substantially removing air bubbles from the liquid medium, the removing means being placed before a patient interface.

25. The removable pumping unit of claim 1, further comprising a patient interface in fluid communication with the outlet port to direct fluid from said chamber to a patient.

26. The pumping system of claim 14, further comprising valve means in fluid connection with the outlet port of the chamber for substantially ensuring unidirectional flow of the liquid medium, the valve means being placed before a patient interface.

27. The pumping system of claim 14, further comprising means in fluid connection with the outlet port of the chamber for substantially removing air bubbles from the liquid medium, the removing means being placed before a patient interface.

28. The pumping system of claim 14, further comprising a patient interface in fluid communication with the outlet port to direct fluid from the chamber to a patient.

* * * * *